United States Patent [19]

Grimes

[11] Patent Number: 4,753,233
[45] Date of Patent: Jun. 28, 1988

[54] NASAL CANNULA

[75] Inventor: Jerry L. Grimes, Chino, Calif.

[73] Assignee: Advantage Medical, Calimesa, Calif.

[21] Appl. No.: 12,837

[22] Filed: Feb. 10, 1987

[51] Int. Cl.$^4$ ............... A61M 15/08; A61M 11/00; A62B 7/00

[52] U.S. Cl. ............... 128/207.18; 604/94; 128/203.22

[58] Field of Search ............... 128/207.18, 203.22, 128/203.23; 604/94

[56] References Cited

U.S. PATENT DOCUMENTS

| | | | |
|---|---|---|---|
| 4,278,082 | 7/1981 | Blackmer | 128/207.18 |
| 4,367,735 | 1/1983 | Dali | 128/207.18 |

FOREIGN PATENT DOCUMENTS

| | | | |
|---|---|---|---|
| 368973 | 2/1923 | Fed. Rep. of Germany | 128/203.22 |
| 533956 | 3/1922 | France | 128/203.22 |
| 174607 | 3/1961 | Sweden | 128/207.18 |

Primary Examiner—William E. Kamm
Assistant Examiner—George Manuel
Attorney, Agent, or Firm—Blakely, Sokoloff, Taylor & Zafman

[57] ABSTRACT

A low bulk nasal cannula providing consistent gas delivery with greater comfort for the patient is described. The cannula of the present apparatus is made of very soft vinyl material to provide greater comfort. The present apparatus utilizes two extending prongs from a central housing to provide gas to nasal passages. Formed on the end of each prong is a laterally hollowed cylindrical post with a convex excurvated tip. This tip allows the cannula to "float" in the nares of the patient's nose to provide proper positioning of the cannula without requiring a "pinch" fit. Since the tips are only formed on one side of each prong, occlusion of the nasal passages during inhaling and exhaling is substantially reduced. The prongs of the cannula are coupled to a cylindrical hollow housing for providing access to the gas source. A firm plastic ridge is formed along the length of the housing and orthogonal to the extended prongs. A thin wire is inserted into the base of the housing and, in conjunction with the firm ridge, provides adjustability to the cannula for a customized fit for a variety of users. The cannula of the present apparatus may be advantageously utilized with a single supply line looping around one ear of the patient. The supply line contacting the patient's face may be made much more lightweight and flexible than the main gas supply line. This further adds to the comfort of the patient when utilizing the cannula of the present apparatus.

7 Claims, 1 Drawing Sheet

NASAL CANNULA

BACKGROUND OF THE INVENTION

1. Field of the Invention

This invention relates to the field of apparatus for providing a gas such as oxygen to the breathing passages of a user.

2. Background Art

Certain diseases or injuries may cause a patient to require prolonged administration of oxygen or other gases. For example, someone afflicted with lung emphezema or a bedridden patient in a hospital, nursing home, etc., may require the administration of oxygen or some other gas to maintain the patient's breathing or for some other therapeutic purpose.

One method of administering therapeutic oxygen to a patient is the use of a nasal cannula. In a nasal cannula, there is provided some means to direct a stream of gas (e.g. oxygen) into the nares of the patient requiring gas. The nares is a cavity formed in the inner nasal passage of a patient. Typically, nasal cannulae employ a pair of tubes or nozzles that project into the nares and are in turn connected to a gas supply which continuously provides the desired gas to the patient's nasal passages.

Generally, nasal cannulea have been placed on the patient so as to be positioned between the patient's upper lip and nostrils. The cannula is held in place by means of a strap extending around the patient's head. The strap may be comprised of the oxygen supply line itself or a separate means such as for example elastic. One such cannula is illustrated in U.S. Pat. No. 3,513,844.

Another method of maintaining the position of the nasal cannula is shown in U.S. Pat. No. 4,278,082. In this method, the oxygen supply lines are looped behind a patient's ears and joined beneath the patient's chin where a cinching means is used to tighten the supply lines, producing tension and securing the cannula in place.

Regardless of the method of attachment, cannula which are positioned in such a manner invariably lead to irritation, potential infection and/or ulceration of the patient's tissue. There is also a great deal of discomfort and inconvenience, particularly in talking or eating, when the device is rigidly held in place. If there is no give to the positioning straps, head movement, eating and talking will result in an increase or decrease in tension, resulting in increased irritation or improper positioning of the cannula. Further, the bulk of prior art nasal cannulae tend to be heavy, conspicuous and uncomfortable.

In order to minimize the irritant effect on the skin between the nostrils and upper lip of a patient, the prior art has attempted to hold the cannula in place by means of a pressure fit within the nasal passages of the nose itself. One such method is illustrated in Swedish Pat. No. 174,607. However, such an approach results in traumatization of the sensitive tissues in the nasal passages and in addition, the tips utilized to provide such a fit also often result in occlusion of the nasal passages during exhaling and inhaling.

Therefore, it is an object of the present invention to provide a nasal cannula in which no head straps are required to maintain the cannula in position.

It is another object of the present invention to provide a nasal cannula having less bulk resting on the patient's face than prior art nasal cannulae.

It is yet another object of the present invention to provide a nasal cannula which will also maintain proper alignment and fit.

It is still another object of the present invention to provide a nasal cannula which does not create pressure trauma or irritation of the patient's face or nasal passages.

It is yet still another object of the present invention to provide a nasal cannula which provides greater comfort to the patient while still insuring consistent delivery of gas to the patient.

SUMMARY OF THE PRESENT INVENTION

A low bulk nasal cannula providing consistent gas delivery with greater comfort for the patient is described. The cannula of the present invention is made of very soft vinyl material to provide greater comfort. The present invention utilizes two extending prongs from a central housing to provide gas to nasal passages. Formed on the end of each prong is a laterally hollowed cylindrical post with a convex excurvated tip. This tip allows the cannula to "float" in the nares of the patient's nose to provide proper positioning of the cannula without requiring a "pinch" fit. Since the tips are only formed on one side of each prong, occulusion of the nasal passages during inhaling and exhaling is substantially reduced. The prongs of the cannula are coupled to a cylindrical hollow housing for providing access to the gas source. A firm plastic ridge is formed along the length of the housing and orthogonal to the extended prongs. A thin wire is inserted into the base of the housing and, in conjunction with the firm ridge, provides adjustability to the cannula for a customized fit for a variety of users. The cannula of the present invention may be advantageously utilized with a single supply line looping around one ear of the patient. The supply line contacting the patient's face may be made much more lightweight and flexible than the main gas supply line. This further adds to the comfort of the patient when utilizing the cannula of the present invention.

DETAILED DESCRIPTION OF THE PRESENT INVENTION

An improved nasal cannula which reduces tissue abrassion of the patient's face and nasal passages while maintaining proper fit and alignment is described. In the following description, numerous specific details, such as type of gas, number of openings, etc., are described in order to provide a more thorough understanding of the present invention. It will be obvious, however, to one skilled in the art, that the present invention may be practiced without these specific details. In other instances, well known features have not been described in detail in order not to unnecessarily obscure the present invention.

Figure 1:
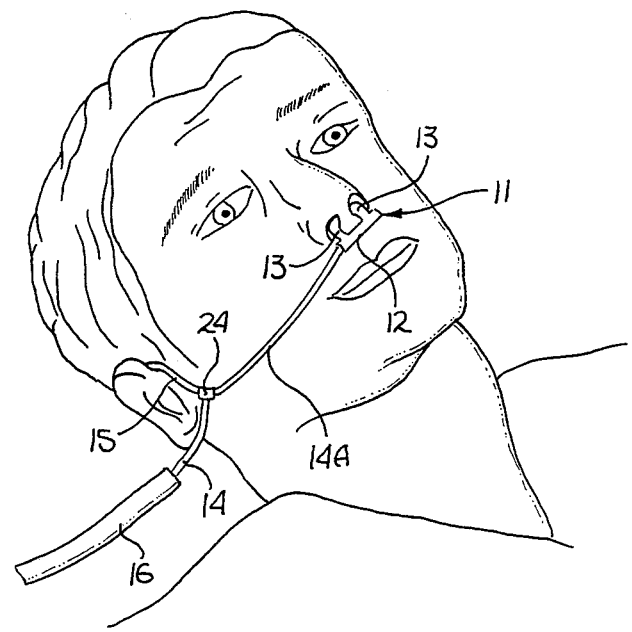
FIG. 1 illustrates the preferred embodiment of the present invention in place on a patient's face.

Referring to FIG. 1, the novel cannula of the present invention is shown in place on a patient's face 10 and is generally indicated by the numeral 11. The cannula 11 comprises a lower housing 12 and extended nozzle members 13 shown disposed in the nasal passages of the patient. A supply tube 14 provides gas to the cannula 11.

For purposes of example, the cannula of the present invention will be described with respect to providing of oxygen gas, $O_2$, to a patient. It will be obvious, however, that the cannula of the present invention can be used to introduce any type of gas or fluid to a patient as desired.

A primary supply tube 16 is coupled to a gas source (e.g. $O_2$) in order to provide oxygen for delivery to the patient through the cannula. At some point between the gas source and the patient, the primary supply line 16 is coupled to supply line 14. In the preferred embodiment of the present invention, supply line 14 is a light weight and flexible plastic tubing. This tubing may be loosely looped around ear 15 and cinched in place with a suitable fastening means such as clip 24. Due to the novel properties of the cannula of the present invention, there is no need to provide tension in either the loop around the patient's ear or that section of supply line 14 between the ear and nose of the patient. That section, designated section 14A in FIG. 1, may have sufficient slack so as not to interfere with normal movement of the patient and in particular when eating, talking or moving the head from side to side. Because the supply line 14A does not need to be taut, there is a reduced risk of irritation and abrasion of the patient's face and correspondingly an increase in comfort to the patient. It also eliminates the need for head straps, and the lightweight tubing employed results in less bulk hanging on the patient's face. Further, pressure, trauma or irritation over the ears is substantially eliminated and the device has a more cosmetic appearance than prior art cannulae.

Figure 2:
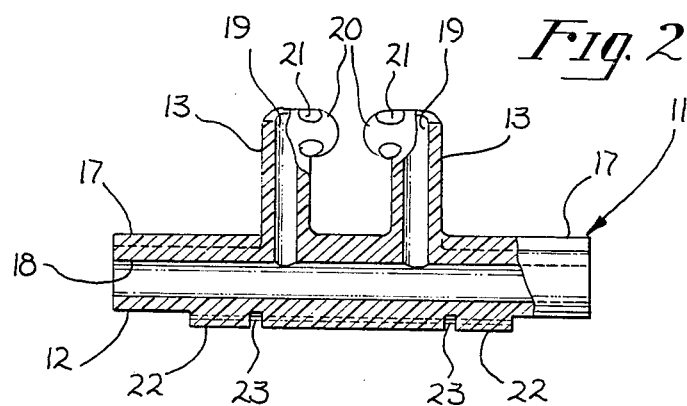
FIG. 2 is a cross sectional view of the nasal cannula of the present invention.
Figure 4:
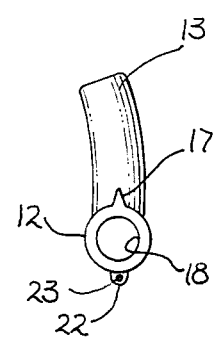
FIG. 4 is an end view of the nasal cannula of FIG. 2.
Figure 3:
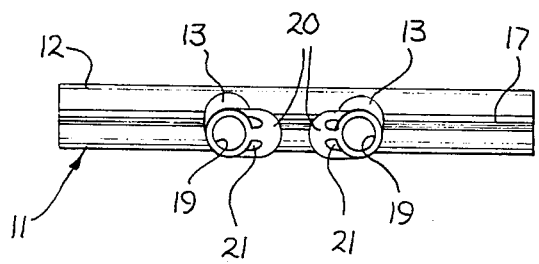
FIG. 3 is a top view of the present invention of FIG. 2.

The cannula of the present invention is shown in detail in FIGS. 2–4. Referring first to FIG. 2, a cross sectional front view of the cannula 11 of the present invention is shown. The housing 12 of the present invention is a generally cylindrical hollow tube made, in the preferred embodiment of the present invention, of soft vinyl material. A bore 18 is formed in housing 12 and may extend the length thereof. In one embodiment of the present invention, one end of housing 12 remains closed off so that a single supply line may be utilized with the cannula open. In other instances, it may be desired to extend bore 18 completely through cannula 11 so that an oxygen supply line may be inserted into the cannula from each end thereof.

A pair of nozzles 13 extends approximately perpendicularly to housing 12 and are comprised of the same vinyl material. In the preferred embodiment, the cannula of the present invention is formed as an integral unit. Nozzles 13 include bores 19 formed therethrough providing fluid communication to central bore 18 of housing 12.

As previously discussed, prior art cannulas are held in place by pressure applied to the housing to hold it in place between the patient's lip and nose, or by a pressure fit within the nasal passages themselves. The present invention avoids the problems associated with both prior art methods and is positioned in the nose of a patient through means of tips 20 formed on each of the nozzles 13. These tips 20 allow the cannula of the present invention to "float" in the nares. The tips of the cannula fit into the natural anatomic space between the nares found in all individuals. By floating with the nares, the tips of the cannula of the present invention do not clip or press against the bridge of the nose. As previously noted, the housing of the cannula of the present invention does not press against the patient's skin so the only point of contact is between the tips 20 and the nares of the patient. A beneficial advantage of this configuration is that as the cannula is worn and becomes moistened with the natural fluids within the nasal passages, the tips 20 of the cannula become moistened and perform as lubricated ball bearings, creating a comfortable fit to the patient without internal trauma.

The tips 20 of the present invention are laterally hollowed cylindrical posts with a convex excurvated tip. The tips 20 include openings 21 therethrough to further reduce the weight of the tip.

The tips 20, extending on only one side of each of the nozzles 13, reduce the possibility of occulusion of the nasal passages during inhaling an exhaling. Particularly during inhaling, air passages become narrower. The use of pressure fit type cannulas requires the use of a "full ball" or "half ball" design. During inhaling, these designs produce an occuluding effect which not only creates an uncomfortable feeling for the patient, but changes the percentage intake of oxygen and air delivered to the patient, effecting the prescribed and proper mixture of gas and air in a negative manner.

In addition to reducing the mass and weight of the cannula of the present invention, openings 21 and tips 20 further relieve the problems associated with occulusion during inhaling. The size of the nozzles and tips of the cannula of the present invention is such so as to still permit the introduction of ambient air to the patient when inhaling.

In order to permit the spacing between the tips 20 of the cannula 11 to be adjusted for the comfort of individual patients, the preferred embodiment of the present invention utilizes a deformable spine 23 in conjunction with a rigid ridge member 11. For patients with narrow spacing between the nares, the tips 20 can be moved closer together so as to allow a proper fit and retention of the cannula in the nose. For patients with larger spaces between the nares, the tips 20 can be separated so as to avoid all pinching of the bridge of the nose while still allowing a proper and comfortable fit to the patient.

In the preferred embodiment of the present invention, a mounting collar 22 formed on the outside of housing 12 substantially opposite nozzles 13 is employed. A stainless steel metal wire is inserted as deformable spine 23 into the mounting collar 22 and extends the length thereof. Although the preferred embodiment of the present invention utilizes a stainless steel wire, as deformable spine 23 any deformable material which retains its shape after deformation may be utilized. In addition, the spine 23 may be mounted directly within the housing 12 if desired or the cannula may be formed with the wire in place.

A ridge 17 is formed on the upper surface of cannula 11 substantially opposite the mounting collar 22. The ridge 17 is comprised of the same material as the cannula 11 but is formed so as to be substantially triangular shaped in cross section (see FIG. 4) and aids in stablizing the cannula in conjunction with deformation of the spine 23. The ridge 17 provides stiffness to the upper surface of the cannula 11 without the need for an additional wire insert. This further reduces the weight and mass of the cannula while still allowing the proper stiffness, flexibility and adjustability of the cannula itself.

The use of the spine 23 and ridge 17 allow the use of very soft material in the remainder of the cannula 11 so that the improved fit and comfort of the present invention may be achieved. If desired, the spine 23 may be preformed into a curved shape to increase the comfort to the patient by allowing the housing to conform more closely to the curvature of the patient's face between the lip and nose.

Thus, a novel nasal cannula resulting in increased comfort to the patient with reduced tissue irritation and trauma has been described.

I claim:

1. A nasal cannula comprising:
   a housing having a central bore therein for coupling said cannula to a gas source;
   first and second substantially parallel nozzles extending substantially orthogonally to said housing, each of said nozzles having a bore formed therethrough in fluid communication with said central bore;
   each of said nozzles having a laterally hollowed cylindrical post having a convex excurvated tip formed thereon and adjacent one end thereof, said post for retaining said cannula in a nares of a user, said post floating in said nares;
   whereby said nasal cannula then may be retained in place by a user without the use of headstraps or pressure fit tips.

2. The nasal cannula of claim 1 wherein said cannula is comprised of soft vinyl.

3. The nasal cannula of claim 1 further including a deformable spine coupled to said housing and a rigid ridge formed on said housing opposite said spine, said spine and said ridge permitting deformation of said cannula to adjust the fit of said cannula for individual users.

4. The nasal cannula of claim 3 wherein said deformable spine comprises stainless steel wire.

5. A nasal cannula comprising:
   a housing having a central bore therein for coupling said cannula to a gas source;
   first and second substantially parallel nozzles extending substantially orthogonally to said housing, each of said nozzles having a bore formed therethrough in fluid communication with said central bore;
   each of said nozzles having a laterally hollowed cylindrical post having a convex excurvated tip formed thereon adjacent one end thereof, said post for retaining said cannula in a nares of a user, said post floating in said nares;
   a deformable spine coupled to said housing substantially opposite said nozzles;
   a rigid ridge formed on said housing substantially opposite said deformable spine, said deformable spine and said ridge allowing said cannula to be deformed to provide proper fit for individual users.

6. The nasal cannula of claim 5 wherein said deformable spine comprises stainless steel.

7. The nasal cannula of claim 5 wherein said cannula is comprised of soft vinyl.

* * * * *